(12) United States Patent
Gao et al.

(10) Patent No.: US 8,679,772 B2
(45) Date of Patent: Mar. 25, 2014

(54) IMMUNOASSAY

(75) Inventors: Zhiqiang Gao, Nanos (SG); Jie Zhang, Nanos (SG)

(73) Assignee: Agency for Science, Technology and Research, Singapore (SG)

( * ) Notice: Subject to any disclaimer, the term of this patent is extended or adjusted under 35 U.S.C. 154(b) by 518 days.

(21) Appl. No.: 12/996,609

(22) PCT Filed: Jun. 6, 2008

(86) PCT No.: PCT/SG2008/000205
§ 371 (c)(1),
(2), (4) Date: Apr. 12, 2011

(87) PCT Pub. No.: WO2009/148406
PCT Pub. Date: Dec. 10, 2009

(65) Prior Publication Data
US 2011/0189705 A1      Aug. 4, 2011

(51) Int. Cl.
*G01N 33/53*        (2006.01)
(52) U.S. Cl.
USPC ......... 435/7.91; 435/7.1; 435/7.9; 435/283.1; 435/287.1; 435/287.2
(58) Field of Classification Search
USPC .......... 435/7.1, 7.9, 7.91, 283.1, 287.1, 287.2
See application file for complete search history.

(56) References Cited

U.S. PATENT DOCUMENTS

| | | | |
|---|---|---|---|
| 5,391,272 A | | 2/1995 | O'Daly et al. |
| 5,443,701 A | * | 8/1995 | Willner et al. ............. 205/777.5 |

(Continued)

FOREIGN PATENT DOCUMENTS

| WO | WO 03/025257 | 3/2003 |
|---|---|---|
| WO | WO 2006/109311 | 11/2006 |

OTHER PUBLICATIONS

International Search Report dated Aug. 28, 2008, issued in related International Patent Application No. PCT/SG2008/000205, filed Jun. 6, 2008.

(Continued)

*Primary Examiner* — Melanie Y Brown
(74) *Attorney, Agent, or Firm* — Kilpatrick Townsend & Stockton LLP (57) ABSTRACT

The invention provides a highly sensitive immunoassay for detection of a biological species. The immunoassay comprises exposing an electrode to an analyte liquid putatively containing the biological species so as to couple the biological species, if present in the analyte liquid, to a binding antibody on the electrode. The electrode comprises a binding antibody and an anchor group, each being coupled to an electrically conductive substrate, said binding antibody being capable of binding to the biological species and said anchor group being capable of binding to a redox polymer. The electrode is then exposed to an antibody-enzyme liquid comprising an antibody-enzyme species, said antibody-enzyme species comprising a detection antibody capable of binding to the biological species, said detection antibody being coupled to a redox enzyme, whereby, if the analyte liquid comprises the biological species, the redox enzyme couples to the electrode by means of the coupling of both the detection antibody and the binding antibody to the biological species. The electrode is then exposed to a polymer solution comprising the redox polymer and to an enzyme substrate, whereby if the redox enzyme is coupled to the anchor group on the electrode the redox polymer is reduced and couples to the anchor group on the electrode. A voltage is then applied between the electrode and a reference electrode and the electrode is exposed to an oxidizable species, whereby a magnitude of an electric current between said electrode and a reference electrode is indicative of the presence or absence of the biological species.

22 Claims, 6 Drawing Sheets

(56) References Cited

U.S. PATENT DOCUMENTS

| | | | |
|---|---|---|---|
| 5,520,786 A * | 5/1996 | Bloczynski et al. | 204/403.14 |
| 6,214,205 B1 * | 4/2001 | Willner et al. | 205/777.5 |
| 6,281,006 B1 * | 8/2001 | Heller et al. | 435/287.9 |
| 6,638,716 B2 | 10/2003 | Heller et al. | |
| 7,455,756 B2 * | 11/2008 | Choi et al. | 204/403.01 |
| 7,897,360 B2 * | 3/2011 | Song | 435/7.4 |
| 7,943,089 B2 * | 5/2011 | Yang et al. | 422/82.01 |
| 2009/0061524 A1 * | 3/2009 | Rishpon et al. | 436/86 |

OTHER PUBLICATIONS

Stollner et al., "Membrane-immobilized haptoglobin as affinity matrix for a hemoblobin-A1c immunosensor," 2002, Analytica Chimica Acta. vol. 470, No. 2, pp. 111-119.

* cited by examiner

IMMUNOASSAY

This application is the U.S. National Stage entry of International Application No. PCT/SG2008/000205, filed Jun. 6, 2008, the contents of which are herein incorporated by reference in their entirety.

TECHNICAL FIELD

The present invention relates to an immunoassay.

BACKGROUND OF THE INVENTION

It is clinically more desirable to develop low density portable protein detection devices since the need for analyzing a large number of proteins in any one patient is less obvious. Such portable devices would enable clinicians to measure a few key proteins at the point of care such as small clinical laboratories and doctors' offices.

Unlike DNA assays, where high specificities can easily be predetermined by simple to chemical synthesis of the capture probe oligonucleotides and high sensitivity can be realized by employing a polymerase chain reaction (PCR) amplification step, the lack of a proteome-wide bioamplification strategy has been one of the practical bottlenecks to ultrasensitive protein assays. Furthermore, to build a viable protein array one has to choose a surface chemistry that will allow immobilized proteins or protein capturing bioaffinitive agents to retain their structural and biological integrities, and to devise an ultrasensitive and versatile means of measuring the degree of protein binding. Among the wide variety of approaches, sandwich immunoassays with optical detection are the most dominant in protein assays since they do not require the analyzed sample to be labelled. This greatly simplifies sample preparation and shortens assay time. The popularity of sandwich immunoassay advanced greatly in the 1970s with the introduction of enzyme-linked immunosorbant assay (ELISA) by Engvall and Perlman (Engvall, E.; Perlman, P. *Immunochemistry* 1974, 8, 871-874). It has become a standard technology in clinical laboratory.

Although optical detections have primarily been employed in ELISA, electrochemical transducers are more advantageous for such assays owing to their high sensitivity, inherent simplicity, and high portability. Furthermore, for opaque or optically dense matrices electrochemical methods are superior. For example, electrochemical measurements can be made on whole blood without interference from blood cells, other proteins, and fat globules. Electrochemical immunoassays (EIA) have therefore been studied as an attractive alternative to radioassays, fluorometric or colourometric assays. Of the many proposed EIAs, those employing amperometric detections have several distinct advantages over other EIAs, such as straightforwardness and high sensitivity. Traditionally, amperometric detection is carried in solution phase, relying on enzyme-mediated solution phase reaction for the formation of electroactive solution phase species. Due to dilution effect, detection limits were usually at ng/mL levels, which are inferior to ELISAs with the optical detections. To lower the detection limit of EIA, various amplification strategies, such as substrate-recycling, the use of nanoparticulate tags, adoption of DNA amplification techniques, including rolling circle amplification and biobarcode-based PCR, interdigitated array electrode, microfluidic devices, and magnetic beads have been proposed to improve the performance of EIA. For example, the biobarcode technology offers PCR-like sensitivity for proteins.

Nonetheless, new schemes, featuring improvements in simplicity, sensitivity or both and based on coupling the biocatalytic amplification of enzyme tags with additional to amplification units and processes are highly desired for meeting the high sensitivity demands of electrochemical detection of proteins.

OBJECT OF THE INVENTION

It is the object of the present invention to substantially overcome or at least ameliorate one or more of the above disadvantages. It is a further object to at least partially satisfy the above need.

SUMMARY OF THE INVENTION

In a first aspect of the invention there is provided an immunoassay for detection of a biological species, said immunoassay comprising the steps of:
a) providing an electrode comprising a binding antibody and an anchor group, each being coupled to an electrically conductive substrate, said binding antibody being capable of binding to the biological species and said anchor group being capable of binding to a redox polymer;
b) exposing the electrode to an analyte liquid putatively containing the biological species so as to couple the biological species, if present in the analyte liquid, to the binding antibody on the electrode;
c) exposing the electrode to an antibody-enzyme liquid comprising an antibody-enzyme species, said antibody-enzyme species comprising a detection antibody capable of binding to the biological species, said detection antibody being coupled to a redox enzyme, whereby, if the analyte liquid comprises the biological species, the redox enzyme couples to the electrode by means of the coupling of both the detection antibody and the binding antibody to the biological species;
d) exposing the electrode to a polymer solution comprising the redox polymer and to an enzyme substrate, whereby if the redox enzyme is coupled to the biological species on the electrode the redox polymer is reduced and couples to the anchor group on the electrode; and
e) applying a voltage between the electrode and a reference electrode and exposing the electrode to an oxidisable species, whereby a magnitude of an electric current between said electrode and a reference electrode is indicative of the presence or absence of the biological species.

The following options may be used in conjunction with the first aspect, either individually or in any suitable combination.

The electrode may be washed between step b) and step c) or between step c) and step d) or between step d) and step e), or at any two of these times, optionally at each of these times, so as to remove species that are not coupled to the electrode.

The electrically conductive substrate may comprise a metal substrate. The metal may be selected from the group consisting of gold, platinum and palladium and mixtures of any two or all of these:

The binding antibody may be coupled to the metal substrate by means of a thiol-containing species. The anchor group may be coupled to the metal substrate by means of a thiol-containing species.

The anchor group may comprise an imidazole group.

The antibody-enzyme species may comprise a complex between a biotinylated detection antibody and an avidin-redox enzyme conjugate.

The redox polymer may comprise a bound transition metal. The transition metal may be osmium. The osmium may be present as an $[Os(4,4'\text{-dimethyl-2,2'-bipyridine})_2Cl]^{2+}$ complex. The transition metal may be complexed to an imidazole group in the polymer.

The polymer may comprise a poly(4-vinylimidazole-co-acrylamide).

The redox enzyme may be an enzyme to which the redox polymer may be used as an artificial mediator. The enzyme substrate is a substrate for the redox enzyme. It may be oxidisable by the redox enzyme. The redox polymer may be such that oxidation of the enzyme substrate by the redox enzyme leads to reduction of the redox polymer. The redox polymer may comprise a bound transition metal such that oxidation of the enzyme substrate by the redox enzyme leads to reduction of the bound transition metal. The redox enzyme may be for example glucose oxidase, and in this event the enzyme substrate may be glucose.

The oxidisable species may comprise ascorbic acid. It may be an electrooxidisable species. It may be a species that may be electrooxidised under catalysis by a reduced form of the redox polymer.

The voltage between the electrode and the reference electrode may be a constant voltage. It may be a voltage of about 0.1 to about 0.5V. The voltage may be such that the oxidisable species is oxidised (for example electrooxidised) in the presence of a reduced form of the redox polymer under the influence of said voltage. The oxidation of the oxidisable species may give rise to an electric current.

The immunoassay may comprise measuring a reference electric current before addition of the oxidisable species and a test electric current after addition of the oxidisable species. The absence of the biological species may be indicated by the test electric current being about the same as the reference electric current. The presence of the biological species may be indicated by the test electric current being greater than the reference electric current. The immunoassay may comprise determining a concentration of the biological species in the analyte liquid from the test electric current and the reference electric current.

The biological species may be a protein.

Step a) may comprise preparing the electrode, said preparing comprising the steps of:

a1) providing an electrode precursor comprising a linking species coupled to the electrically conductive substrate, said linking species comprising a binding group which is capable of binding to the antibody and is capable of binding to the linking species;

a2) coupling the antibody to the linking species; and a3) coupling the anchor group to the linking species.

The binding group may be an activated ester.

Step a1, above, may comprise coupling a thiol-containing species comprising a carboxylic acid to the electrically conductive substrate, and reacting the carboxylic acid to form the activated ester.

In an embodiment there is provided an immunoassay for detection of a biological species, said immunoassay comprising the steps of:

a) providing an electrode comprising a binding antibody and an imidazole group, each being coupled to a gold substrate, said binding antibody being capable of binding to the biological species;

b) exposing the electrode to an analyte liquid putatively containing the biological species so as to couple the biological species, if present in the analyte liquid, to the binding antibody on the electrode;

c) exposing the electrode to an antibody-enzyme liquid comprising a complex between a biotinylated detection antibody and an avidin-glucose oxidase conjugate, whereby, if the analyte liquid comprises the biological species, the glucose oxidase couples to the electrode;

d) exposing the electrode to a polymer solution comprising a redox polymer comprising poly(4-vinylimidazole-co-acrylamide) complexed to an $[Os(4,4'\text{-dimethyl-2,2'-bipyridine})_2Cl]^{2+}$ complex and also exposing the electrode to glucose, whereby if the glucose oxidase is coupled to the imadazole group on the electrode the $[Os(4,4'\text{-dimethyl-2,2'-bipyridine})_2Cl]^{2+}$ complex is reduced and couples the polymer to the anchor group on the electrode; and e) applying a voltage between the electrode and a reference electrode and exposing the electrode to an oxidisable species, whereby a magnitude of an electric current between said electrode and a reference electrode is indicative of the presence or absence of the biological species.

In a second aspect of the invention there is provided an electrode for use in an immunoassay for detection of a biological species, said electrode comprising a binding antibody and an anchor group, each being coupled to an electrically conductive substrate, said binding antibody being capable of binding to the biological species and said anchor group being capable of binding to a redox polymer.

The electrically conductive substrate may comprise a metal substrate. The metal may be selected from the group consisting of gold, platinum and palladium and mixtures of any two or all of these.

The binding antibody may be coupled to the metal substrate by means of a thiol-containing species. The anchor group may be coupled to the metal substrate by means of a thiol-containing species.

The anchor group may comprise an imidazole group.

In an embodiment there is provided an electrode for use in an immunoassay for detection of a biological species, said electrode comprising a binding antibody and an imidazole group, each being coupled to a gold substrate by means of a thiol-containing species, said binding antibody being capable of binding to the biological species.

The invention also provides an electrode according to the second aspect, wherein the binding antibody of said electrode is bound to the biological species. Thus it provides an electrode for use in an immunoassay for detection of a biological species, said electrode comprising a binding antibody and an anchor group, each being coupled to an electrically conductive substrate, said binding antibody being bound to the biological species and said anchor group being capable of binding to a redox polymer.

The invention also provides an electrode according to the second aspect, wherein the binding antibody of said electrode is bound to the biological species and an antibody-enzyme species is coupled to the biological species. Thus it provides an electrode for use in an immunoassay for detection of a biological species, said electrode comprising a binding antibody and an anchor group, each being coupled to an electrically conductive substrate, said binding antibody being bound to the biological species and said anchor group being capable of binding to a redox polymer, wherein an antibody-enzyme species is coupled to the biological species, said antibody-enzyme species comprising a detection antibody capable bound to the biological species, said detection antibody being coupled to a redox enzyme.

The invention also provides an electrode according to the second aspect, wherein the binding antibody of said electrode is bound to the biological species, an antibody-enzyme species is coupled to the biological species, and a redox polymer is coupled to the anchor group. Thus it provides an electrode for use in an immunoassay for detection of a biological species, said electrode comprising a binding antibody and an anchor group, each being coupled to an electrically conductive substrate, said binding antibody being bound to the biological species and said anchor group being bound to a reduced form of a redox polymer, wherein an antibody-enzyme species is coupled to the biological species, said antibody-enzyme species comprising a detection antibody capable bound to the biological species, said detection antibody being coupled to a redox enzyme.

In a third aspect of the invention there is provided a process for making an electrode for use in an immunoassay for detection of a biological species, said process comprising:
  i) providing an electrode precursor comprising a linking species coupled to the electrically conductive substrate, said linking species comprising a binding group which is capable of coupling to a binding antibody and is capable of coupling to an anchor group, said binding antibody being capable of binding to the biological species and said anchor group being capable of binding to a redox polymer;
  ii) coupling the antibody to the linking species; and
  iii) coupling the anchor group to the linking species.

Step i may comprise coupling a thiol-containing species comprising a carboxylic acid to the electrically conductive substrate, and reacting the carboxylic acid to form an activated ester. The anchor group may comprise an imidazole group.

In an embodiment there is provided a process for making an electrode for use in an immunoassay for detection of a biological species, said process comprising:
  i) coupling a thiol-containing species comprising a carboxylic acid to an electrically conductive substrate, and reacting the carboxylic acid to form an activated ester;
  ii) coupling the antibody to the activated ester; and
  iii) coupling the anchor group to the activated ester.

In another embodiment there is provided a process for making an electrode for use in an immunoassay for detection of a biological species, said process comprising:
  i) coupling an α,ω-mercaptocarboxylic acid to a gold substrate;
  ii) converting the carboxylic acid group of said am-mercaptocarboxylic to an activated ester group (e.g. an sulfosuccinimide ester);
  iii) coupling an antibody binding group to the activated ester group, said antibody binding group being capable of binding to a binding antibody capable of binding to the biological species;
  iv) coupling an imidazole group to the activated ester group; and
  v) binding the binding antibody to the antibody binding group.

The invention also provides an electrode for use in an immunoassay for detection of a biological species, said electrode being made by the process of the third aspect. There is also provided the use of an electrode according to the second aspect, or made according to the third aspect, for detection of a biological species.

In a fourth aspect of the invention there is provided a kit for conducting an immunoassay, said kit comprising:
  a first part comprising an electrode according to the second aspect of the invention;
  a second part comprising an antibody-enzyme species, optionally in solution; and
  a third part comprising a redox polymer, optionally in solution.

The kit may also comprise instructions describing how to perform the immunoassay. The immunoassay may be according to the first aspect of the invention. The antibody-enzyme species may be as described earlier.

The invention also provides the kit of the fourth aspect when used for conducting an immunoassay, or for determining the presence, absence or concentration of a biological species.

In a fifth aspect of the invention there is provided a system for conducting an immunoassay, said system comprising:
  an electrode according to the second aspect of the invention;
  a counterelectrode electrode;
  a reference electrode; and
  a source of electrical current; and
  a current measuring device;
wherein the three electrodes are coupled to the source of current so as to be able to set the potential of the working electrode with respect to the reference electrode at a selected value by passing a current between the electrode according to the second aspect and the working electrode.

The source of electrical current may be capable of applying a steady voltage. The source of electrical current may comprise a potentiostat. The current measuring device may comprise an ammeter. The current measuring device may be coupled to a calculating device, e.g. a computer, for determining the presence, absence or concentration of a biological species from a current measured by said measuring device.

BRIEF DESCRIPTION OF THE DRAWINGS

A preferred embodiment of the present invention will now be described, by way of an example only, with reference to the accompanying drawings wherein:

FIG. 2 shows (A) Cyclic voltammograms of a complete electrode at 100 mV/s in PBS (1) before and (3) after adding 5.0 mM AA to the PBS; (2) a control electrode after adding 5.0 mM AA. (B) Corresponding amperometric responses of (1), (2), and (3).

FIG. 3 shows graphs illustrating (A) Effect of PVIA-Os concentration on the deposition of PVIA-Os; (B) Effect of AA concentration on the oxidation current in amperometry of (1) a complete electrode and (2) a control.

DETAILED DESCRIPTION OF THE INVENTION

The present invention relates to an improved immunoassay for detection of a biological species. Biological species which may be detected by the immunoassay include any species capable of having two antibody species attached thereto simultaneously. These include proteins, whole cells, viruses, DNA, DNA fragments etc.

The immunoassay utilises an electrode comprising a binding antibody and an anchor group. These are each coupled to an electrically conductive substrate. They may be coupled to the same face, or same side, of the conductive substrate. They may be coupled such that each binding antibody is near an anchor group, optionally adjacent an anchor group. They may be interspersed on the conductive substrate. Once made, the electrode may be stored prior to use. Suitable storage temperatures are below about 10° C., or less than about 9, 8, 7, 6 or 5° C., or about 0 to about 10° C., or about 0 to 5, 0 to 2, 2 to 10, 5 to 10 or 3 to 5° C., e.g. about 0, 1, 2, 3, 4, 5, 6, 7, 8, 9 or 10° C. Thus the electrode may be stable at the above temperatures. It may be stable at said temperature for at least about 1 week, or at least about 2, 3, 4, 5, 6, 7, 8, 9 or 10 weeks.

The substrate may comprise a metal substrate or may comprise a non-metallic electrically conductive substrate to which the binding antibody and the anchor group can be attached, either directly or through a linking species. Suitable substrates include gold, platinum and palladium and mixtures of any two or all of these. These substrates are known to bind strongly to thiols and other sulphur species (thiocarboxylic acids, disulfides etc.), which may therefore serve as a linking species. Where mention is made herein to thiols, this also includes the corresponding thiocarboxylic acids, disulfides or other sulphur species capable of binding to gold, platinum or palladium.

The electrically conductive substrate may be laid down on a primary substrate, which may be conductive, non-conductive (i.e. insulating) or semiconducting. A suitable primary substrate is glass. The electrically conductive substrate may be laid down directly on the primary substrate, or an adhesion layer may be interposed between the two. A suitable adhesion layer for the above-mentioned metal substrates is titanium. The adhesion layer may be about 1 to about 10 nm thick, or about 1 to 5, 1 to 2, 2 to 10, 5 to 10, 2 to 5 or 2.5 to 5=thick, e.g. about 1, 1.5, 2, 2.5, 3, 3.5, 4, 4.5, 5, 6, 7, 8, 9 or 10 nm thick. It may for example be laid down by electron-beam evaporation. Thus the primary substrate may have the electrically conductive substrate laid down by means of electrodeposition, electron-beam evaporation, sputtering, precipitation or some other suitable method, either directly or on an adhesion layer. The electrically conductive substrate may be between about 50 and about 200 nm thick, or about 50 to 100, 100 to 200, 75 to 100 or 100 to 150 nm thick, e.g. about 50, 75, 100, 125, 150, 175 or 200 nm thick. It may represent an electrically conductive layer on the primary substrate.

It may be advantageous to anneal the resultant structure (primary substrate plus electrically conductive substrate, optionally with intervening adhesion layer) following formation, particularly in the event that the adhesion layer (if present) and the electrically conductive substrate are both metallic. Suitable annealing conditions are about 200-300° C. for about 1 to 5 hours (in particular about 250° C. for about 3 hours). In order to ensure the cleanliness of the electrically conductive layer prior to attachment of subsequent species thereto, the electrically conductive layer may be cleaned. This may use a cleaning agent, e.g. an oxidising and/or acidic solution such as "piranha" solution. A cleaning agent should be used that does not corrode or degrade the electrically conducting substrate or the primary substrate or, if present, the adhesion layer. Following the cleaning, the electrically conductive substrate should be carefully rinsed so as to remove the cleaning agent from the electrically conductive substrate. This avoids interaction between the cleaning agent and subsequent species that are applied thereto.

Suitable linking species include activated esters of mercaptocarboxylic acids, e.g. of $\alpha,\omega$-mercaptocarboxylic acids. The hydrocarbon chain (i.e. the chain connecting the carboxylic acid group to the thiol group) of the mercaptocarboxylic acid may be straight chain or branched chain. It may have a main chain of between 6 and 16 carbon atoms, or 6 to 10, 10 to 16 or 8 to 14 carbon atoms, e.g. about 6, 7, 8, 9, 10, 11, 12, 13, 14, 15 or 16 carbon atoms. The activated ester may be a sulfosuccinimide ester, or a nitrophenyl ester or a pentafluorophenyl ester.

The linking species may be applied to the electrically conductive substrate by exposing the electrically conductive substrate to a solution of the linking species in a suitable solvent. Suitable solvents include lower alcohols such as ethanol, methanol, propenol or isopropanol. The solution may be about 1 to about 10 mM in the linking species, or about 1 to 5, 1 to 2, 2 to 10, 5 to 10 or 2 to 5 mM. The solvent should be capable of dissolving the linking species and is preferably miscible in water so that it may be readily rinsed from the surface of the electrode using water. The exposing commonly comprises immersing the electrode in the solution, but may comprise spraying the solution on the electrode or flowing the solution over or past the electrode. It is known that thiols readily couple at room temperature to certain metal surfaces, such as gold, platinum and palladium. Thus for a substrate comprising one of these metals, exposure to a mercaptocarboxylic acid linking species is an effective means of coupling. Once the linking species has been coupled to the electrode surface, and preferably unreacted solution has been rinsed off, a carboxylic acid function of the linking species may be to converted to an activated ester. This may be accomplished by reacting with a suitable hydroxyfunctional reagent, optionally in the presence of a catalyst or coreagent. Suitable catalysts/coreagents include known esterification catalysts/coreagents such as carbodiimides. Examples include 1-ethyl-3,(3-dimethylaminopropyl)carbodiimide and dicyclohexylcarbodiimide. Suitable hydroxyfunctional reagents include N-hydroxysulfosuccinimide (NHS), p-nitrophenol and pentafluorophenol. This reaction may be conducted in water, in which case water soluble reagents and catalysts/coreagents are preferred.

Following formation of the electrode precursor, i.e. the substrate having the linking species thereon, the binding antibody is coupled to the linking species. This may be accomplished by applying the binding antibody in solution to the electrode precursor. The solution may be about 0.01 to about 1 mg/ml in antibody, or about 0.01 to 0.5, 0.01 to 0.1, 0.01 to 0.05, 0.05 to 1, 0.1 to 1, 0.5 to 1, 0.05 to 0.5, 0.05 to 0.2 or 0.05 to 0.1 mg/ml, e.g. about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.6, 0.7, 0.8, 0.9 or 1 mg/ml. The solution is commonly an aqueous solution, although the solvent may be any suitable solvent that does not denature the antibody. A common solvent is PBS (phosphate buffered saline). This step generally does not result in binding of an antibody molecule to every linking species on the electrode precursor. Exposure of the antibody-reacted electrode precursor to an anchor group species therefore couples the anchor group to at least some of the remaining unreacted sites. Suitable anchor groups are those which can couple to a redox polymer, in particular to the reduced form of a redox polymer. The anchor group may be capable of complexing with a transition metal in the polymer, in particular to the reduced form of the transition metal. Suitable anchor groups include imidazole groups, amines, pyridine groups, or other nitrogen containing moieties. Thus suitable anchor group species comprise the anchor group coupled to a functional group capable of reacting with the activated ester group. These include for example aminofunctional imidazoles, such as aminoalkyl imidazoles. The ratio between anchor groups to binding antibodies on the electrode surface may be about 1:100 and about 1:1, or about 1:100 and 1:2, 1:100 and 1:5, 1:100 and 1:10, 1:100 and 1:20, 1:10 and 1:50, 1:50 and 1:1, 1:20 and 1:1, 1:10 and 1:1, 1:5 and 1:1, 1:2 and 1:1, 1:50 and 1:5, 1:50 and 1:10, 1:20 and 1:5 or 1:20 and 1:10, e.g. about 1:100, 1:90, 1:80, 1:70, 1:60, 1:50, 1:40, 1:30, 1:20, 1:15, 1:10, 1:9, 1:8, 1:7, 1:6, 1:5, 1:4, 1:3, 1:2 or 1:1 on a molar or weight basis.

The binding antibody is capable of binding to the biological species to be assayed by the immunoassay. Thus the biological species is an epitope, optionally an antigen, for the binding antibody. The binding antibody may be capable of binding said biological species to the substrate. The binding antibody should be capable of being coupled to the substrate, optionally by means of a linking species, without loss of its ability to selectively couple to the biological species. Suitable linking species are described above.

The term "antibody" as used herein includes IgG (including IgG1, IgG2, IgG3, and IgG4), IgA (including IgA1 and IgA2), IgD, IgE, IgM, and IgY), and is intended to include whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin. Antigen-binding antibody fragments, including single-chain antibodies, may comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies may be monoclonal, polyclonal, chimeric, humanized, and human monoclonal and polyclonal antibodies which specifically bind a marker.

The anchor group is capable of binding to a redox polymer. It may be capable of binding to a redox polymer on reduction of said redox polymer. It may be capable of binding to the redox polymer by complexing with a transition metal on said redox polymer. It may be capable of binding the redox polymer to the substrate. It may be incapable of binding to said redox polymer prior to reduction thereof. It may be capable of binding to a reduced form of said redox polymer. It may be capable of selectively binding to a reduced form of said redox polymer. The redox polymer may comprise a complexed transition metal. The anchor group may be capable of complexing with the reduced form of said transition metal. The anchor group may comprise an imidazole group.

The transition metal may be osmium, ruthenium, platinum, iron, or some other suitable transition metal. The transition metal may be present as a bis(bipyridine) complex. It may be present as a complex comprising at least one labile ligand. The labile ligand may be a halide, e.g. Cl. In the event that the transition metal is osmium, the oxidised state of the osmium may be the $3^+$ state. In the reduced state the osmium may be present in a $2^+$ state. The osmium may be present in the polymer as an $[Os(4,4'-dimethyl-2,2'-bipyridine)_2Cl]^{2+}$, $[Os(2,2'-bipyridine)_2Cl_2]Cl$, $(Os(bpy)_2Cl2)$, $[Os(4,4'-dimethyl-2,2'-bipyridine)_2Cl_2]Cl$, $(Os(dmbpy)_2)$, $[Os(4,4'-diamino-2,2'-bipyridine)_2Cl_2]Cl$ $(Os(dabpy)_2)$, $[Os(dimethylbipyridine)(terpyridine)Cl)]Cl2$, or $(Os(bpy)(tpy))$ complex, or some other complex. The transition metal may be complexed to an imidazole group in the polymer, or to some other group capable of complexing the transition metal, for example an amine, a pyridine, or some other suitable nitrogen containing moiety. The group capable of complexing the transition metal may be a terminal group (e.g. endgroup). It may be a non-terminal group. It may be attached to the main chain of the polymer. It may be attached to a side chain of the polymer. The polymer may be a homopolymer or it may be a copolymer. It may be a straight chain polymer. It may be a branched polymer. It may be a hyperbranched polymer. It may be a comb polymer. It may be a water soluble polymer. It may comprise monomer units which comprise groups capable of complexing the transition metal. It may comprise imidazole groups. It may comprise 4-vinylimidazole monomer units. It may comprise a polymer or copolymer of 4-vinylimidazole. It may comprise a poly(4-vinylimidazole-co-acrylamide), (PVIA), poly(vinylpyridine-co-acrylamide), poly(vinylimidazole-co-acrylic acid), poly(vinylimidazole-co-acrylamido-2-methyl-1-propanesulfonic acid), poly(vinylpyridine-co-acrylamido-2-methyl-1-propanesulfonic acid), or a mixture of any two or more of these. The polymer, or the bound transition metal thereof, in its reduced form may be capable of catalysing the electrooxidation of the oxidisable species. In the present immunoassay, catalysis of electrooxidation of the oxidisable species by the bound polymer (or by the bound transition metal thereof) on the electrode leads to a current flow if the biological species is present.

In the immunoassay of the invention, the electrode, comprising a binding antibody and an anchor group each coupled to the electrically conductive substrate, is exposed to an analyte liquid putatively containing the biological species. The exposing may comprise at least partially, optionally completely, immersing the electrode in the liquid, passing (e.g. spraying, flowing etc.) the liquid over or past the electrode or some other form of exposing. Since the binding antibody is selected so that the biological species is an epitope of the binding antibody, if the biological species is present in the analyte liquid, the binding antibody will couple the biological species to the binding antibody, thereby immobilising the biological species on the electrode. If the biological species is not present in the analyte liquid, the electrode will be unaffected. The exposing may be for sufficient time to effect binding of the antibody to the biological species (if present). It may be for at least about 5 minutes, or at least about 10, 15, 20, 25, 30, 40, 50 or 60 minutes, or may be for about 5 minutes to about 2 hours, or about 5 minutes to 1 hour, 5 to 45 minutes, 5 to 30 minutes, 5 to 15 minutes, 15 minutes to 2 hours, 30 minutes to 2 hours, 1 to 2 hours, 15 minutes to 1 hour, 15 to 30 minutes or 30 to 60 minutes, e.g. about 5, 10, 15, 20, 25, 30, 35, 40, 45, 50 or 55 minutes, or 1, 1.2, 1.4, 1.6, 1.8 or 2 hours, or may be for more than 2 hours. The exposing is commonly at about room temperature.

The electrode is then exposed to an antibody-enzyme liquid comprising an antibody-enzyme species. The antibody-enzyme species comprises a detection antibody capable of binding to the biological species, said detection antibody being coupled to a redox enzyme, for example glucose oxidase. The redox enzyme should be one to which the redox polymer may be used as artificial mediator. Thus in the event that the biological species was present in the analyte liquid, and thereby was immobilised on the electrode in the previous step, the detection antibody is coupled to the electrode (by means of the biological entity) and thereby the redox enzyme is coupled to the electrode and immobilised thereon. The detection antibody may be the same as the binding antibody, or it may be different thereto, provided that both of said antibodies are capable of simultaneously coupling to the same biological species. This step of exposing may comprise at least partially, optionally completely, immersing the electrode in the antibody-enzyme liquid, passing (e.g. spraying, flowing etc.) the liquid over or past the electrode or some other form of exposing. The exposing may be for sufficient time to effect binding of the antibody to the biological species (if present). It may be for at least about 5 minutes, or at least about 10, 15, 20, 25, 30, 40, 50 or 60 minutes, or may be for about 5 minutes to about 2 hours, or about 5 minutes to 1 hour, 5 to 45 minutes, 5 to 30 minutes, 5 to 15 minutes, 15 minutes to 2 hours, 30 minutes to 2 hours, 1 to 2 hours, 15 minutes to 1 hour, 15 to 30 minutes or 30 to 60 minutes, e.g. about 5, 10, 15, 20, 25, 30, 35, 40, 45, 50 or 55 minutes, or 1, 1.2, 1.4, 1.6, 1.8 or 2 hours, or may be for more than 2 hours. The exposing is commonly at about room temperature.

The antibody-enzyme species comprises both the detection antibody and redox enzyme, both being in a form in which they can perform their normal function. A convenient means to form the antibody-enzyme species is by use of the avidin-biotin pair or the streptavidin-biotin pair, which are well known to form stable complexes. Thus the antibody may be biotinylated and the redox enzyme conjugated to avidin or streptavidin. These two species may then be coupled to form the antibody-enzyme species. Other means to couple the detection antibody to redox enzyme may also be used, for example redox enzyme-antibody conjugates, aptamer-redox enzyme conjugates, peptide-redox enzyme conjugates, etc.

Commonly the electrode will then be washed in order to remove any unreacted antibody-enzyme species. The electrode is then exposed to a polymer solution comprising the redox polymer and to the enzyme substrate. If the biological species was present in the analyte solution, the detection antibody will have been coupled to the biological species, which in turn will have been immobilised on the electrode. The redox enzyme will then have coupled to the electrode via the detection antibody. In this event the redox enzyme will oxidise the enzyme substrate, and thereby reduce the redox polymer (in a particular embodiment reduce the transition metal on the redox polymer). On reduction of the redox polymer, it is then capable of coupling to the anchor group on the electrode. Thus a common embodiment of this reaction involves reduction of the transition metal on the polymer, leading to loss of a ligand therefrom. This enables a ligand, e.g. an imidazole group, of the anchor group to complex with the transition metal, leading to coupling of the polymer to the electrode.

A voltage is then applied between the electrode and a reference electrode and the electrode is exposed to an oxidisable species. In the event that the redox polymer is present on the electrode surface (which indicates the presence of the biological species in the original analyte solution), oxidation of the oxidisable species will lead to current flow between the electrode and the reference electrode. The magnitude of this current is indicative of the presence or absence of the biological species. The voltage is commonly about 0.1 to about 0.5V, or about 0.1 to 0.3, 0.3 to 0.5 or 0.2 to 0.4V, e.g. about 0.1, 0.15, 0.2, 0.25, 0.3, 0.35, 0.4, 0.45 or 0.5V. It may be a constant voltage. The oxidisable species may be any suitable species, commonly organic species, which is capable of being oxidised by the redox polymer under the applied voltage. It may be a carboxylic acid. It may be ascorbic acid. Other suitable substrates which may be electrooxidised under catalysis by the redox polymer according to the present invention include hydrazine, amines, NADH (the reduced form of nicotinamide adenine dinucleotide), FAD (flavin adenine dinucleotide), etc.

Commonly after one or more steps of the immunoassay the electrode will be washed in order to remove unreacted species. Suitable washing liquids include aqueous liquids such as water and PBS. The washing may comprise immersing the electrode in the washing liquid. It may comprise flowing the washing liquid over or past the electrode. It may comprise multiple (e.g. 2, 3, 4, 5, 6, 7, 8, 9 or 10) washing steps. The washing liquid should not contain the species to be removed, and should be preferably be capable of dissolving said species. The electrode precursor may be washed after coupling the binding antibody thereto. It may be washed after coupling the anchor group thereto. The electrode may be washed after exposure to the analyte solution. It may be washed after exposure to the antibody-enzyme liquid. It may be washed after coupling to the redox polymer. The washing liquid used in each washing step may be the same or may be different.

Commonly the immunoassay comprises measuring an electric current before (reference) and after (test) addition of the oxidisable species between the electrode and a reference electrode. Commonly a 3-electrode system is used. Thus the electrode of the present invention is used as the test electrode. A reference electrode, e.g. Ag/AgCl, and a counterelectrode, e.g. platinum wire, are also used. The current measurement is conveniently conducted in PBS as supporting electrolyte. Alternatively, a reference current may be measured separately, e.g. in PBS containing no oxidisable species. A subsequent test current may then be measured in PBS containing the oxidisable species. If the biological species was not present in the analyte solution, there will be no bound redox polymer on the electrode, as described above. Consequently there will be no catalytic oxidation of the oxidisable species catalysed by the polymer. As a result the current will be the same in the presence or absence of the oxidisable species. Thus if no biological species was present in the analyte solution, this will be indicated by the test electric current being about the same as the reference electric current. By similar logic, the presence of the biological species will be indicated by the test electric current being greater than the reference electric current, due to the oxidation of the oxidisable species catalysed by the electrode bound redox polymer. The concentration of the biological species in the analyte liquid may be determined from the test electric current and the reference electric current. By comparing the difference between these two currents, and comparing that difference with a calibration curve obtained from known concentrations of the biological species, the concentration in the analyte solution may be determined.

An ultrasensitive electrochemical immunoassay for the detection of proteins is therefore described herein. In an embodiment the assay involves utilizing enzyme-catalyzed deposition of a redox polymer and electrocatalytic oxidation of ascorbic acid by the deposited redox polymer: a dual amplification scheme to enhance analytical signal. Capture antibody was covalently immobilized on a self-assembled 11-mercaptoundecanoic acid (MUA) monolayer coated gold electrode. After incubating with a target protein (antigen), the gold electrode was treated in biotinylated detection antibody and avidin-glucose oxidase conjugate solution. Thereafter, the electrode was dipped in an aqueous solution of poly(4-vinylimidazole-co-acrylamide) partially imidazole-complexed with $[Os(bmpy)_2Cl]^{2+}$ (bmpy=4,4'-dimethyl-2,2'-bipyridine). Upon the addition of glucose, the redox polymer was enzymatically reduced and deposited on the electrode surface via ligand-exchange with anchoring sites. The deposited redox polymer exhibited excellent electrocatalytic activity towards the oxidation of ascorbic acid. Consequently, the concentration of protein could be quantified amperometrically. This electrochemical immunoassay combined the specificity of the immunological reaction with the sensitivity of the dual-amplified electrochemical detection.

Advantages of the present invention include
rapid and ultrasensitive detection of proteins.
the method is highly sensitive and no analyte protein labeling is needed.
the redox polymer tag used in the invention displays high reactivity. For example, the Os-containing redox polymer exhibits high electron mobility and good kinetics, and effectively activates the enzyme labels.

an achievable detection limit of femtograms of protein for a cancer biomarker carcinoembryonic antigen.

good specificity, for example, it selectively and directly detects the analyte in the serum.

can be easily integrated in a microelectromechanical system (MEMS) and fully automated Micro-Total Analysis System (μ-TAS).

low cost and high potential of multiplexing and mass production.

The presently described immunoassay may have a lower detection limit of less than about 10 pg/ml of the biological species, or less than about 5, 2, 1, 0.5, 0.2 or 0.1 pg/ml (or a detection limit of about 10, 9, 8, 7, 6, 5, 4, 3, 2, 1 0.9, 0.8, 0.7, 0.6, 0.5, 0.4, 0.3, 0.2 or 0.1 pg/ml). It may be capable of quantifying with acceptable accuracy concentrations over a range of about 1 to about 10,000 pg/ml of the biological species, or about 1 to 5,000, 1 to 2,000, 1 to 1,000, 1 to 500, 1 to 200, 1 to 100, 2 to 10,000, 10 to 10,000, 100 to 10,000, 500 to 10,000, 1,000 to 10,000, 2 to 5,000, 2 to 1,000 or 10 to 1,000 pg/ml.

DETAILED DESCRIPTION OF THE PREFERRED EMBODIMENTS

Disclosed herein is an adaptation of a double-amplification scheme in EIA to further enhance the sensitivity and lower the detection limit. The applicability of the system in protein detection was demonstrated with an important colon cancer biomarker, carcinoembryonic antigen (CEA). In contrast to previous EIAs, by enzymatically depositing a redox polymer (the second amplifier, the enzyme tag glucose oxidase (GOx) being the first amplifier) on an electrode surface and subsequently utilizing the deposited redox polymer as an electrocatalyst for the oxidation of ascorbic acid (AA), proteins may be conveniently detected amperometrically. More importantly, the assay sensitivity and detection limit are markedly improved and are superior to the solution phase EIA. Detection limits are comparable to the best optical and radioimmunoassays.

An ultrasensitive electrochemical immunoassay for the detection of proteins is described herein. The assay involves utilizing enzyme-catalyzed deposition of a redox polymer and electrocatalytic oxidation of ascorbic acid by the deposited redox polymer, a double amplification scheme to enhance analytical signals. Capture antibody and redox polymer anchoring agent were covalently immobilized on a gold electrode coated with a 11-mercaptoundecanoic acid monolayer. After incubating with a target protein (antigen), the electrode was treated in biotinylated detection antibody and avidin-glucose oxidase conjugate solution. Thereafter, it was dipped in an aqueous solution of a redox polymer. Upon the addition of glucose, the redox polymer is enzymatically reduced and deposited on the electrode surface. The deposited redox polymer exhibits excellent electrocatalytic activity towards the oxidation of ascorbic acid. Consequently, the concentration of the target protein could be quantified amperometrically.

This electrochemical immunoassay combines the specificity of the immunological reaction with the sensitivity of the double-amplified electrochemical detection. The applicability of the assay was demonstrated with an important colon cancer biomarker, carcinoembryonic antigen (CEA). As little as femtograms of CEA (1.0 pg/mL) was successfully detected.

GOx-catalyzed deposition of redox polymer. The fabrication of the electrode for uses in EIA requires a series of surface chemical reactions. These steps are as follows:

(1) formation of a self-assembled monolayer of MUA, (2) reaction of the MUA monolayer with EDC-NHS, (3) covalent attachment of antibody onto the electrode and (4) treatment of the unreacted sites with a redox polymer anchoring agent, API.

In step 1, a monolayer of MUA is self-assembled onto the gold substrate. All data obtained indicated a single molecular layer of MUA coated on the gold electrode. In step 3, antibody is covalently attached to the surface of the MUA monolayer. The use of chemical coupling approach, instead direct physical adsorption, has three distinct advantages:

(i) it provides much better stability of the immobilized protein, (ii) it avoids the nonspecific adsorption of protein onto the bare gold electrode, and (iii) the surface coverage of mAb can be manipulated to optimize conditions for protein binding.

In the final step of the electrode fabrication, the unreacted sites of the electrode were utilized as anchoring points by reacting with API to create a surface that is highly reactive to the deposition of the redox polymer.

QCM was first used to investigate the immunoreaction and the redox polymer deposition characteristics. Redox polymers comprising [osmium(2,2'-bipyridine)$_2$Cl$_2$]Cl (Os(bpy)$_2$), [osmium(4,4'-dimethyl-2,2'-bipyridine)$_2$Cl$_2$]Cl, (Os(dmbpy)$_2$), [osmium(4,4'-diamino-2,2'-bipyridine)$_2$Cl$_2$] Cl (Os(dabpy)$_2$), or [Os(dimethylbipyridine)$_2$(terpyridine) Cl)]Cl, (Os(bpy)(tpy)) and different polymer backbones, namely, poly(vinylimidazole-co-acrylamide) (PVIA), poly (vinylpyridine-co-acrylamide), poly(vinylimidazole-co-acrylic acid), poly(vinylimidazole-co-acrylamido-2-methyl-1-propanesulfonic acid), and poly(vinylpyridine-co-acrylamido-2-methyl-1-propanesulfonic acid) were tested for their abilities to form stable deposits during GOx catalyzed reduction in PBS containing glucose and the redox polymer. It was observed that PVIA gives the highest redox polymer loading amongst the polymer backbones studied. Only PVIA was subsequently used for the preparation of various redox polymers. A serious of QCM measurements were carried out after immunoreactions and after the redox polymer deposition, with the BSA coated gold electrode as control. The results are summarized in Table 1. As shown in Table 1, 35 ng of CEA was captured. Treatment of the electrode with the mAb-GOx conjugate solution resulted in an approximately 60 ng increase in mass loading. This number represents about 70% of the surface-bound CEA was actually reacted with the second antibody. It is not possible to attach mAb-GOx to every captured CEA due to steric hindrance and bulky nature of the mAb-GOx conjugate. The surface coverage of mAb-GOx loaded onto the electrode was found to be about $1.0 \times 10^{-12}$ mole/cm$^2$ (geometrical area 0.20 cm$^2$, roughness factor 1.3). This value corresponds to about 60% of a random, densely packed GOx monolayer on the electrode surface. To attain the highest sensitivity and best reproducibility, the mAb-GOx tagging process was optimized to ensure maximal GOx loading.

TABLE 1

QCM Data of after reaction to 10 ng/mL CEA mAb-GOx labeling, and after a 30 min-incubation in 10 mg/mL redox polymer solution.

| Redox polymer (10 mg/mL) | CEA (10 ng/mL) | | mAb-GOx (1.0 ng/mL) | | Redox polymer deposition (10 mg/mL) | | |
|---|---|---|---|---|---|---|---|
| | Δf (Hz) | Δm (ng) | Δf (Hz) | Δm (ng) | Δf (Hz) | Δm (ng) | Loading (×10$^{10}$ mole/cm$^2$) |
| PVIA-Os(bpy)$_2$ | 39 | 35 | 65 | 58 | 7.6 | 6.8 | 1.6 |
| PVIA-Os(dabpy)$_2$ | 38 | 34 | 71 | 64 | 11 | 10 | 2.4 |
| PVIA-Os(dmbpy)$_2$ | 41 | 37 | 67 | 60 | 24 | 22 | 5.8 |
| PVIA-Os(bpy)(tpy) | 37 | 33 | 66 | 59 | ~0.0 | ~0.0 | ~0.0 |

As for the redox polymer deposition, it was found that only those containing at least one labile ligand in the Os(bpy)$_2$ moiety, such as inner-sphere chloride, are able to deposit on the electrode. Redox polymers without halide, such as PVIA-complexed with [Os(bpy)(tpy)]$^{2+/3+}$ were not deposited (Table 1). The characteristics of the films deposited from aerated and de-aerated solutions were similar, suggesting neither oxygen nor its reduction products affects the deposition of PVIA-Os from a 10 mg/mL solution. Also, of the redox polymers studied, PVIA-Os was the best in terms of stability of the deposit and the amount of redox polymer being deposited on the electrode surface.

It has been observed that the rate of ligand exchange is faster for weakly coordinating ligands of Os(II)/III) such as chloride than it is for strongly coordinating ligands such as imidazole. Also, ligand exchange is much faster in Os(II) complexes than in similar Os(III) complexes, as the electrochemical reduction of Os(III)-bipyridine complexes often results in loss of halide and the replacement by other strong ligands, or even by organic solvent such as acetonitrile when present, although the halide loss appears to occur at a very slow rate for the osmium complexes and usually is not noticeable on the cyclic voltammetry time scale. The deposition of the redox polymer appears to require exchange of an halide of a polymer-bound complex of Os(II)/III) by a surface-bound ligand (anchoring agent). For example, the exchange of chloride of PVIA-Os by the surface-bound imidazole ligand leads to deposition of the redox polymer. Because protein surfaces are rich in lysine and arginine residues, it is likely that these also are the chloride-exchanging functions, i.e. they may act as additional anchoring points. The capture antibody on the electrode surface can therefore serve as an additional anchoring point (multi-anchoring points) as their coordinating functions also exchange inner sphere chloride of [Os(bpy)$_2$Cl]$^{+/2+}$. Furthermore, in water-soluble polymers, having multiple chloride-containing Os(II) complexes upon reduction and also having multiple uncoordinated ligand functions, such as imidazoles or amines, exchange of chloride by ligand can crosslink the polymer, bringing additional stability and further redox polymer to the surface.

There are two processes that may lead to the redox polymer deposition when the electrode is immersed in the glucose/PVIA-Os solution. The first is deposition of PVIA-Os upon reduction by glucose, the second is dehydration of the polymer upon its reduction. The oxidized and reduced redox polycations of the present work differ in their reactivity and solubility, the more positively charged oxidized redox polymer being much more soluble in water and less reactive than its reduced counterpart. Thus, it is thought that the first stage of the deposition process involves chemisorption of the reduced polymer on the electrode surface. Because the reduced redox polymer exchanges ligands and is not as hydrated as its oxidized counterpart, it spontaneously crosslinks. At the same time, in the absence of substantial hydration the segmental mobility is insufficient to allow extensive internal reorientation of the surface-bound film. Only those segments that had appropriately oriented neighbouring pairs of free ligand and chloride are crosslinked.

It had been considered that the redox polymer deposition may be initiated by oxygen reduction, involving the reaction between the reduction product, hydrogen peroxide, or the radical intermediates generated in the process of GOx catalyzed oxygen reduction by glucose. Hydrogen peroxide was ruled out since adding small amounts of hydrogen peroxide to the glucose/PVIA-Os solution showed no effect on the deposition process at all. However, if the deposition is the result of the reaction between the redox polymer and the radical intermediates generated in the reduction of dissolved oxygen, the deposition of PVIA-Os should be substantially slowed down by degassing the solution before introducing the electrode. Experiments showed that similar redox polymer films were obtained in an oxygen-free glucose/PVIA-Os solution, suggesting that oxygen reduction is not part of the polymer film formation process.

Figure 2A:
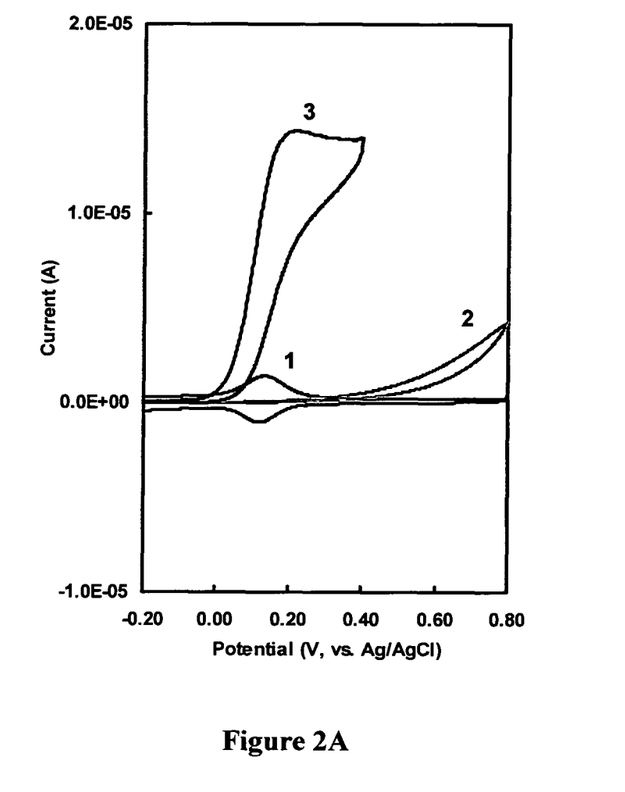

Feasibility of protein detection. In the first attempts of detecting protein utilizing the deposited redox polymer, CEA standard solutions were tested on the working and the control electrode. Upon applying to the working electrode surface at room temperature, CEA in the solution was selectively bound by its antibody and immobilized on the electrode surface. Repeated rinsing with PBS completely washed off all the non-immune reaction related CEA. GOx tags were brought to the electrode surface via biotin-avidin interaction during a subsequent incubation with the second antibody and A-GOx solution. Typical cyclic voltammograms of the completed electrode reacted with CEA in PBS (trace 1) and in 5.0 mM AA (trace 3) are shown in FIG. 2A. As seen in FIG. 2A, in the absence of AA, the only obvious electrochemical process between −0.20 and +0.80 V is the reduction-oxidation of Os(II)/Os(III) couple. Steady-state cyclic voltammograms of the deposited PVIA-Os film at different scan rates showed a typical surface-confined process. The characteristics of the deposited redox polymer matched those of a reversible surface immobilized redox couple. The peak currents increased linearly with the potential scan rate up to 200 mV/s and the ratio of the anodic to the cathodic charge, obtained by integrating the current peaks at a very slow scan rate, were close to theoretical, showing that both the transport of electrons and of counter-ions within the film were rapid. The presence of biological species in the film did not appreciably alter the electrochemistry of the redox polymer. Such results confirm that all of the osmium redox centers are allowed to reach the electrode surface and proceed to reversible heterogeneous electron transfer. The surface electroactive centers (Γ), measured by integrating either the reduction or the oxidation current peak, gave a value of $5.8 \times 10^{10}$ mol/cm$^2$. Because the redox polymer contains about one redox center per $10^3$ daltons and because about 1.2 g·cm$^{-3}$ is a reasonable estimate of their density, the thickness of the deposited films is about 6 nm. At low scan rates the two current peaks were almost mirrored each other, the separations of their peaks ($\Delta$Ep) being <20 mV, close to the theoretical value of 0 mV characteristic of strongly adsorbed monolayers of monomeric redox couples. By contrast, in the much thicker solvent-cast and chemically crosslinked films the current peaks of the reduction and oxidation branches of the voltammograms are separated by >60 mV.

Obvious catalytic current was observed when AA was added, due to the presence of the redox polymer. The Os(d-mpy)$^{2+3+}$ sites of the redox polymer effectively act as a catalyst in the electrochemical oxidation of AA. Moreover, at the applied potential of 0.15V, the thus reduced redox polymer is instantly oxidized electrochemically, forming a substrate-recycling mechanism in the film.

To test for possible oxidation through direct electron-exchange with the substrate electrode, an electrode without applying the redox polymer was fabricated and its voltammogram was measured in PBS containing AA. Comparison of the voltammetry with that of an electrode that was not treated by CEA showed no measurable difference. Furthermore, while AA was catalytically electrooxidized already at a potential as low as 0.15 V vs Ag/AgCl on the electrode with the redox polymer film, electrooxidation of AA was not observed at the control electrode exposed to the AA solution at potentials <0.40V (FIG. 2A trace 2), ruling out the possibility that the oxidation of AA is a direct electron-exchange with the gold electrode.

Figure 2B:
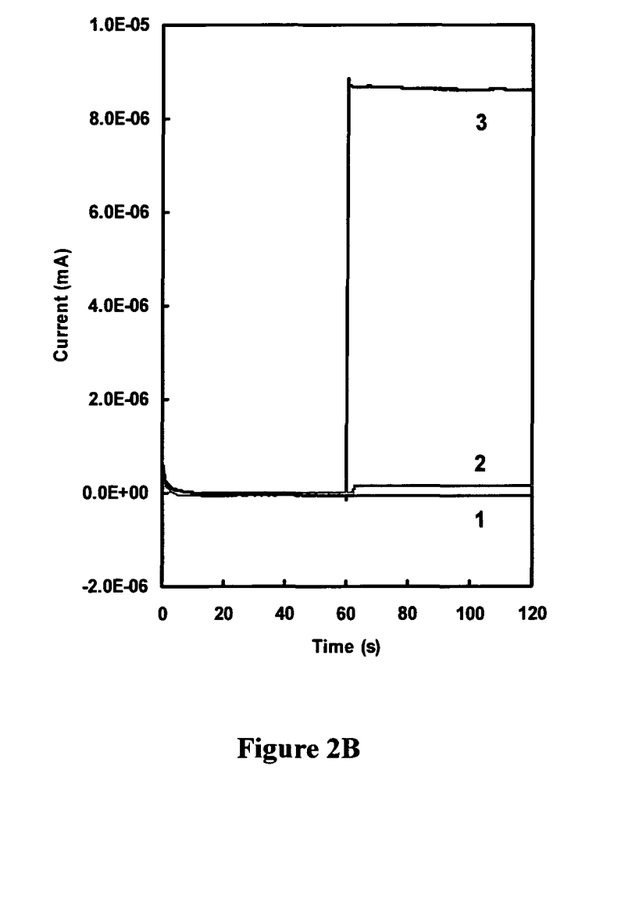

When the completed electrode was immersed in PBS, the oxidation current of AA in amperometry increased by 8.8 $\mu$A at 0.15 V upon adding 5.0 mM AA to PBS (FIG. 2B trace 3), whereas a typical charge current decay was observed without AA (FIG. 2B trace 1). In an identical experiment (control experiment) where BSA was immobilized on the electrode surface, negligible change of current was observed upon the addition of AA (FIG. 2B trace 2). The amperometric results complimented the cyclic voltammetric data obtained earlier and confirmed that CEA was successfully detected with high specificity. Moreover, due to partial protonation of the capture antibody at pH 7.4, some anti-nonspecific adsorption ability is brought to the electrode since the redox polymer is positively charged.

Figure 3:
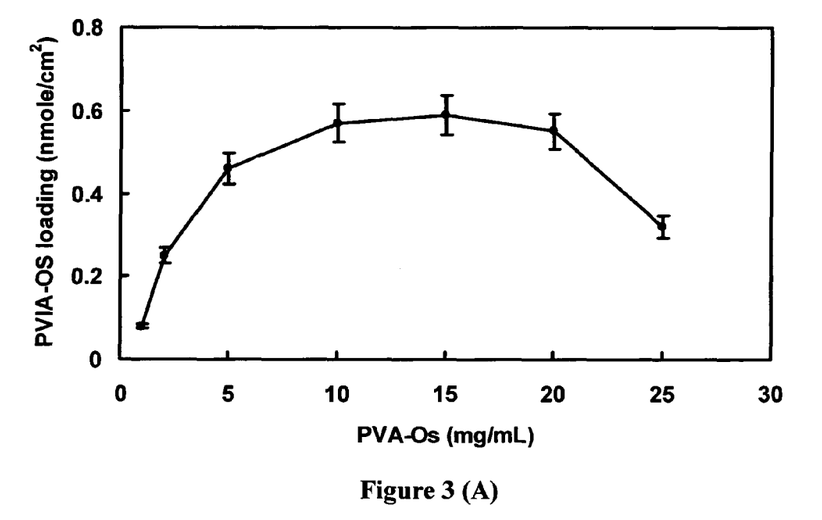

Optimization. FIG. 3A illustrates the dependence of the amount of the deposited redox polymer on the concentration of the PVIA-Os where a high enough glucose concentration 25 mM was maintained throughout. As PVIA-Os concentration increased, the signal rose rapidly and almost linearly at first, and then leveled off until a maximum sensitivity was reached at 10 mg/mL (FIG. 3A). It was observed that the amount of the deposited redox polymer is practically independent of PVIA-Os concentration between 5 and 15 mg/mL. This suggests that the GOx-catalyzed reduction of PVIA-Os is at its maximum rate without any appreciable depletion of the concentration of the oxidized PVIA-Os, and that the PVIA-Os deposition rate is now solely determined by the amount of the reduced redox polymer brought to the electrode surface, which in turn, is determined by the total amount of GOx at the electrode surface, and thus by the concentration of sample protein in solution. At 25 mg/mL of PVIA-Os the redox polymer deposited under identical conditions was about $\frac{2}{3}^{rd}$ of that at 10 mg/mL, possibly due to self-crosslinking among individual polymer chains before they had a chance to react with the surface anchoring groups. The deposition rate increased with increasing glucose concentration and a maximum was attained at concentrations >10 mM, Very high glucose concentrations, e.g. 0.10 M, had very little additional beneficial effect.

As expected, the amperometric signal is strongly dependent on the concentration of AA. When the oxidation potential for Os (II) is sufficient, the overall reaction rate and hence the sensitivity of the system is determined by the apparent catalytic activity of the redox polymer. The oxidation current increased with increasing AA concentration and plateaued beyond 5.0 mM. (FIG. 3B trace 1). It was found that a substantial increase in the AA oxidation current was observed at the control electrode when high AA concentration (>10 mM) was employed, which significantly lower the signal-to-noise ratio (FIG. 3B trace 2).

Figure 4:
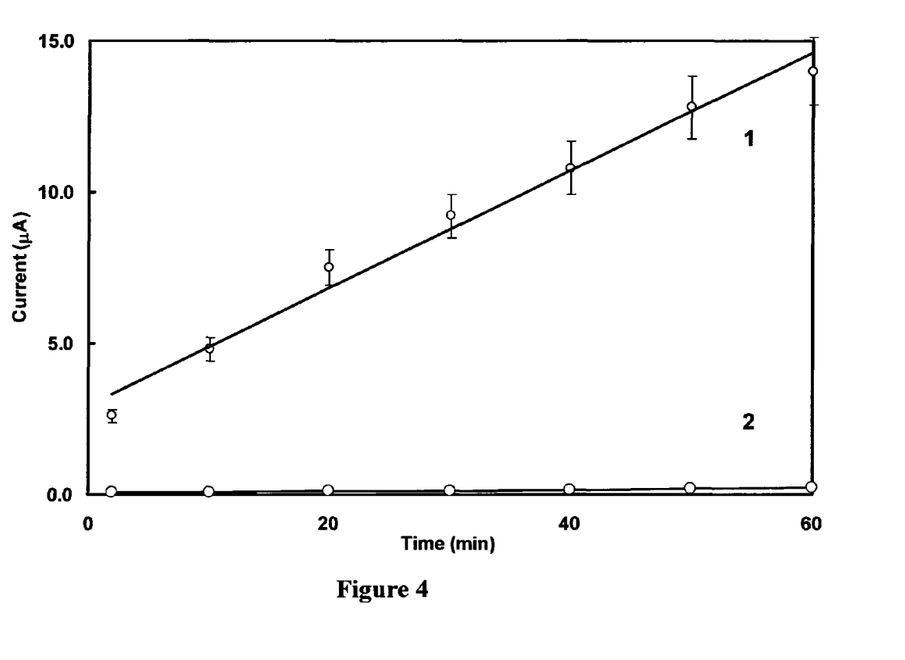
FIG. 4 shows a graph illustrating the effect of incubation time in glucose/PVIA-Os solution on the amperometric response of 5.0 ng/mL CEA. Poised potential: 0.15 V, 5.0 mM AA.

To leverage the cumulative nature of the process for further improving the sensitivity of the method, a series of amperometric tests were conducted. A plot of the AA oxidation current at different incubation times is shown in FIG. 4. In all cases, an immediate increase in the AA oxidation current in amperometry was observed due to the presence of the redox polymer. The sensitivity was proportional to the incubation time throughout, indicating that there was little activity loss of GOx during incubation. However, there is a balance between high sensitivity and assay time. It was found that a 30 min-incubation period was sufficient to detect protein at femtogram levels.

Figure 5:
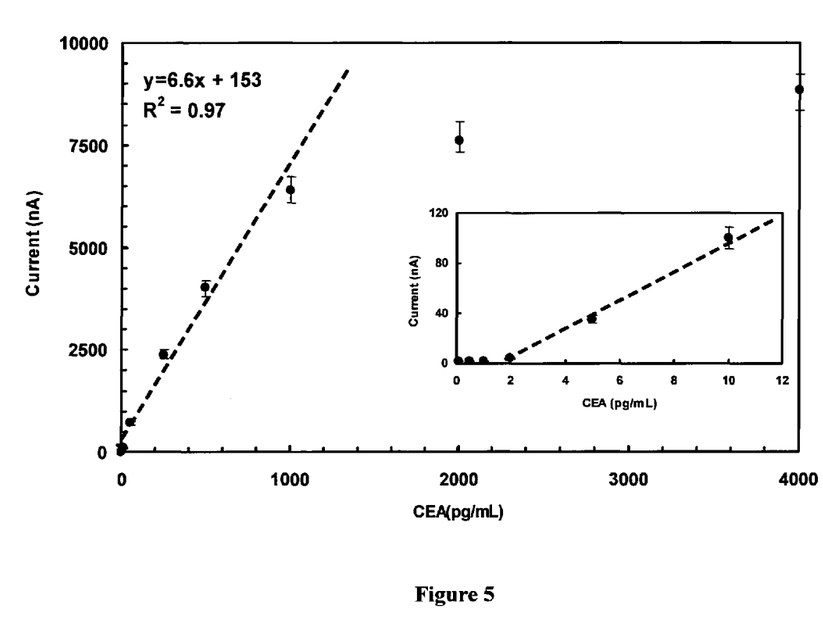
FIG. 5 shows amperometric responses of different CEA concentration in 2.0 droplets. Poised potential: 0.15 V, 5.0 mM AA. Insert: The calibration curve at low concentration end.

Calibration curve for CEA. Utilizing this enzyme catalyzed deposition of the redox polymer and the electrocatalytic oxidation of AA by the redox polymer as the signal amplification method for the detection of proteins, the current in amperometry is primarily dependent on the amount (density) of the redox polymer (electrocatalyst) deposited on the electrode surface when the substrate (AA) concentration is sufficiently high. The more the target protein molecules captured, the more the redox polymer deposited, thus the higher the oxidation current. Since the ratio of the GOx tags to the sample protein molecule is practically constant at high mAb-GOx conjugate concentration, the amount of the capture antibody immobilized on the electrode and immunoreaction efficiency determine the amount of GOx bound to the electrode. It has been shown that under optimized experimental conditions, the redox polymer deposition is a sole GOx-controlled process, implying that the sample protein molecules captured is directly correlated to the AA oxidation current and thus a simple and straightforward linear relationship between the oxidation current and protein concentration can be expected. To construct the calibration curve, 10 measurements were carried out for each concentration to obtain the average of the oxidation current. FIG. 5 shows representative amperometric data obtained from the electrodes treated with solutions of increasing concentrations of CEA. As the concentration of CEA was increased, the AA oxidation current increased accordingly in amperometry. Under optimal experimental conditions, A dynamic range was found to be from 2.0 to 1000 pg/mL with a relative standard derivation of <20% and a detection limit of 1.0 pg/mL estimated from 3-fold of noise. A higher detection limit, 3.0 pg/mL, was observed when working with serum samples. It was found that a practically constant current (saturation current) was observed at a CEA concentration of 10-20 ng/mL. Comparing with the enzymatically catalyzed oxidation of phenolic compounds and subsequent detection of the oxidation product in solution for the detection of proteins, the sensitivity of the present assay is two orders of magnitude higher. In practice, this sensitivity of the assay meets the requirements for direct protein detection in real-world samples.

Conclusions

The results showed that thin films of the redox polymer comprising both ligands and exchangeable inner-sphere chloride complexes of Os(II)/III) can be irreversibly deposited from an aqueous solution under mild conditions catalyzed by GOx. The deposited films exhibited the classical electrochemistry of a surface-confined reversible redox couple and showed excellent catalytic activity towards electrochemical oxidation of AA. It was demonstrated that the introduction of the double-amplification mechanism in EIA offers new possibilities for much improved protein assay. While the concept of the double-amplification has only been illustrated using CEA model analyte, it could be easily extended to a wide range of proteins of clinical, biological and environmental significance. Efforts to fabricate electrochemical protein arrays for multiplexing and incorporate the array into a handheld electrochemical detector are currently underway.

EXAMPLES

Materials and Reagents. Unless otherwise stated, chemicals were obtained from Sigma-Aldrich (St Louis, Mo.) and used without further purification. The redox polymer used in this study was poly(4-vinylimidazole-co-acrylamide) partially imidazole-complexed with $[Os(dmpy)_2Cl]^{2+}$ (PVIA-Os). Synthesis of the redox polymer was described elsewhere. The oxidized form of PVIA-Os was used in the protein detection. To demonstrate the "proof of principle", CEA was selected as the model protein since rabbit polyclonal antibody and monoclonal antibodies to this cancer biomarker are commercially available. CEA (CD66e, molecular weight about 180 KDa) and its monoclonal antibody (mAb, clone C6G9) were purchased from Sigma. The biotinylation of mAb was performed using a known method. Briefly, the mAb solution was dialyzed overnight at 4° C. against 0.10 M sodium bicarbonate buffer, pH 8.3. 200 µl of biotin-N-hydroxysuccinimide ester (2.0 mg/ml) dissolved in dimethyl sulfoxide was added to 1.0 ml aliquots containing 1.0 mg antibody. After a 4-h incubation at room temperature on a rotator, the mixture was centrifuged at 5000 rpm for 10 min to remove any precipitates and then extensively dialyzed against phosphate-buffered saline (PBS) for 24 h at 4° C. with five changes of PBS in between. The dialyzed biotinylated antibody was then stored at −80° C. until use. Avidin-glucose oxidase conjugate (A-GOx) was obtained form victor laboratories (Burlingame, Calif. 94010).

Electrode fabrication. To fabricate the working electrode, a titanium adhesion layer of 25-50 Å was first electron-beam evaporated onto a glass slide followed by 750-1000 Å of gold. It was then annealed at 250° C. in air for 3 h. It was reported that gold evaporation on glass produces large, flat crystallites, with a predominating (111) texture, which is a preferred crystallographic texture for marcaptan self-assembly. Annealing of the gold film further enhances the (111) texture. Before antibody immobilization, the gold coated slide was thoroughly cleaned in a freshly-prepared piranha solution (98% $H_2SO_4$/30% $H_2O_2$=3/1. CAUTION: Piranha solution is a powerful oxidizing agent and reacts violently with organic compounds.) and copiously rinsed with Milli-Q water followed by 10 min sonication in absolute ethanol. The gold surface was then modified immediately after the cleaning step. Initial thiol adsorption was accomplished by immersing the gold substrate in an ethanolic solution of 2.0 mM 11-mercaptoundecanoic acid (MUA) at room temperature. The electrodes were rinsed with Milli-Q water and activated with 100 mM of 1-ethyl-3(3-dimethyl-aminopropyl)-carbodiimide (EDC) and 40 mM of N-hydroxysulfosuccinimide (NHS) in water. A patterned 1-mm thick adhesive spacing/insulating layer was assembled on the top of the slide. The diameter of the individual sensor was 2.0 mm. Aliquots of 0.10 mg/mL mAb in PBS were applied to the electrodes and incubated for 3 h at room temperature. After rinsing with washing buffer (PBS+0.050% Tween-20), the unoccupied MUA sites were treated in 2.0 mM 1(3-aminopropyl)-imidazole (API) in PBS overnight at room temperature. The array was rinsed with washing buffer then stored at 4° C. until used. Bovine serum albumin (BSA) coated electrodes were used as control.

Characterization. Electrochemical experiments were carried out using a CH Instruments Model 660A electrochemical workstation coupled with a low current module (CH Instruments, Austin, Tex.). The three-electrode system consisted of a 2-mm-diameter gold working electrode, a miniature Ag/AgCl reference electrode, and a platinum wire counter electrode. PBS was used as the supporting electrolyte.

Figure 1:
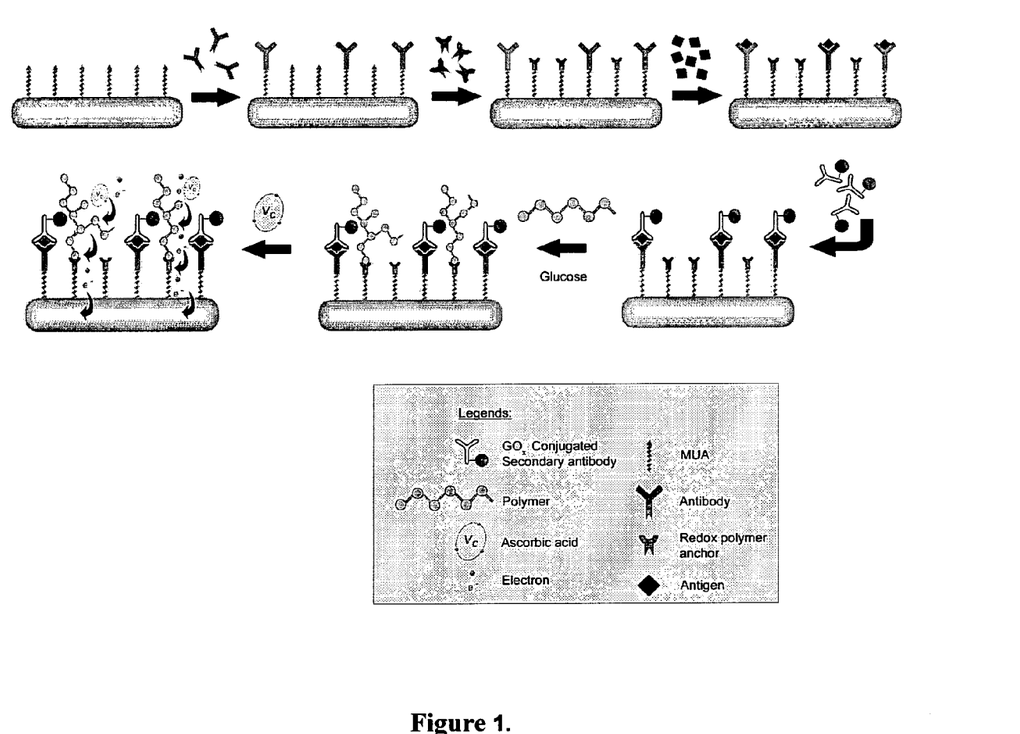
FIG. 1 is a diagrammatic illustration of double-amplified electrochemical enzyme immunoassay.

Immunoreaction and redox polymer deposition were monitored by a quartz crystal microbalance (QCM) cell (CH Instruments Inc. Austin, Tex.) in a clean environment. The frequency responses were stable within 2.0 Hz in air over a period of 30 min. Quartz crystal resonators employed in QCM experiments were 13.6-mm-diameter 10-MHz AT-cut type with 5.11-mm-diameter gold electrodes on both sides, purchased from Fortiming Corp. (Ashland, Mass.). Stable frequency responses were taken after washing off unreacted materials and drying in a stream of air. To minimize variation from electrode to electrode, the same electrode was always used for both immunoreaction and redox polymer deposition. The Sauerbrey equation is used for calculating mass change at the crystal:

$$\Delta f = 2f_0^2 (\mu_q \rho_q)^{-1/2} \Delta m/A \quad (1)$$

where $\Delta f$ is the measured frequency shift in hertz due to mass change, $f_0$ the resonant frequency of the fundamental mode of the crystal, $\mu_q$ the shear modulus of quartz (2.95× $10^{11}$ dyne/$cm^2$), $\rho_q$ the density of the resonator (2.65 g/$cm^3$), $\Delta m$ the mass change of the crystal and A electrode surface area. For the 10 MHz resonator used in this study, Eq. (1) predicts that a frequency change of 1.0 Hz corresponds to a mass change of 0.90 ng on the electrode Protein detection. CEA incubation and its electrochemical detection were carried out in five steps, as depicted in FIG. 1. The electrode was placed in a moisture-saturated environmental chamber. Aliquots of CEA solution (2.0 µL) were placed on the electrode and incubated for 30 min. After washing for 10 min in a vigorously stirred PBS and drying, biotinylated mAb/A-GOx (½, 5.0 µL) was dispensed onto the electrode and incubated for 10 min. The electrode was washed, dried and a glucose-redox polymer mixture solution (10 µL) was applied onto the electrode and incubated for 30 min. The catalytic response was evaluated by amperometry at a constant potential of 0.15 V in PBS containing 5.0 mM AA. In the case of low CEA concentrations, smoothing was applied after each measurement to remove random noises. All incubations and measurements were performed at room temperature. All potentials reported in this work were referred to the Ag/AgCl reference electrode.

The invention claimed is:
1. An immunoassay for detection of a biological species, said immunoassay comprising the steps of:
  a) providing an electrode comprising a binding antibody and an anchor group, each being coupled to an electrically conductive substrate, said binding antibody being capable of binding to the biological species and said anchor group being capable of binding to a redox polymer;

b) exposing the electrode to an analyte liquid putatively containing the biological species so as to couple the biological species, if present in the analyte liquid, to the binding antibody on the electrode;

c) exposing the electrode to an antibody-enzyme liquid comprising an antibody-enzyme species, said antibody-enzyme species comprising a detection antibody capable of binding to the biological species, said detection antibody being coupled to a redox enzyme, whereby, if the analyte liquid comprises the biological species, the redox enzyme couples to the electrode by means of the coupling of both the detection antibody and the binding antibody to the biological species;

d) exposing the electrode to a polymer solution comprising the redox polymer and to an enzyme substrate, whereby if the redox enzyme is coupled to the biological species on the electrode the redox polymer is reduced and couples to the anchor group on the electrode; and e) applying a voltage between the electrode and a reference electrode and exposing the electrode to an oxidisable species, whereby a magnitude of an electric current between said electrode and a reference electrode is indicative of the presence or absence of the biological species.

2. The immunoassay of claim 1 wherein the electrode is washed between step b) and step c), between step c) and step d) and between step d) and step e) so as to remove species that are not coupled to the electrode.

3. The immunoassay of claim 1 wherein the electrically conductive substrate comprises a metal substrate, said metal being selected from the group consisting of gold, platinum and palladium and mixtures of any two or all of these.

4. The immunoassay of claim 3 wherein the binding antibody and the anchor group are coupled to the metal substrate by means of a thiol-containing species.

5. The immunoassay of claim 1 wherein the anchor group comprises an imidazole group.

6. The immunoassay of claim 1 wherein the antibody-enzyme species comprises a complex between a biotinylated detection antibody and an avidin-glucose oxidase conjugate.

7. The immunoassay of claim 1 wherein the redox polymer comprises a bound transition metal.

8. The immunoassay of claim 7 wherein the transition metal is osmium.

9. The immunoassay of claim 8 wherein the osmium is present as an $[Os(4,4'-dimethyl-2,2'-bipyridine)2Cl]^{2+}$ complex.

10. The immunoassay of claim 7 wherein the transition metal is complexed to an imidazole group in the polymer.

11. The immunoassay of claim 7 wherein the polymer comprises a poly(4-vinylimidazole-co-acrylamide).

12. The immunoassay of claim 1 wherein the redox enzyme is glucose oxidase and the enzyme substrate is glucose.

13. The immunoassay of claim 1 wherein the oxidisable species comprises ascorbic acid.

14. The immunoassay of claim 1 wherein the voltage between the electrode and the reference electrode is a constant voltage of about 0.1 to about 0.5 V.

15. The immunoassay of claim 1 comprising measuring a reference electric current before addition of the oxidisable species and a test electric current after addition of the oxidisable species.

16. The immunoassay of claim 15 wherein the absence of the biological species is indicated by the test electric current being about the same as the reference electric current.

17. The immunoassay of claim 15 wherein the presence of the biological species is indicated by the test electric current being greater than the reference electric current.

18. The immunoassay of claim 15 comprising determining a concentration of the biological species in the analyte liquid from the test electric current and the reference electric current.

19. The immunoassay of claim 1 wherein the biological species is a protein.

20. The immunoassay of claim 1 wherein step a) comprises preparing the electrode, said preparing comprising the steps of:

a1) providing an electrode precursor comprising a linking species coupled to the electrically conductive substrate, said linking species comprising a binding group which is capable of binding to the antibody and is capable of binding to the linking species;

a2) coupling the antibody to the linking species; and a3) coupling the anchor group to the linking species.

21. The immunoassay of claim 20 wherein the binding group is an activated ester.

22. The immunoassay of claim 21 wherein step a1 comprises coupling a thiol-containing species comprising a carboxylic acid to the electrically conductive substrate, and reacting the carboxylic acid to form the activated ester.

* * * * *